United States Patent [19]

Neuberger

[11] Patent Number: 5,566,267
[45] Date of Patent: Oct. 15, 1996

[54] FLAT SURFACED OPTICAL FIBERS AND DIODE LASER MEDICAL DELIVERY DEVICES

[75] Inventor: Wolfgang Neuberger, Monchen-Gladbach, Germany

[73] Assignee: Ceram Optec Industries Inc., East Longmeadow, Mass.

[21] Appl. No.: 356,116

[22] Filed: Dec. 15, 1994

[51] Int. Cl.⁶ .................................................. G02B 6/16
[52] U.S. Cl. ................................. 385/123; 385/902
[58] Field of Search .................................. 385/117, 118, 385/123, 125, 133, 146, 147, 902, 126, 127; 372/101

[56] References Cited

U.S. PATENT DOCUMENTS

| | | | |
|---|---|---|---|
| 3,712,705 | 1/1973 | Marcatili | 385/125 |
| 4,068,920 | 1/1978 | Bass et al. | 385/125 |
| 4,089,584 | 5/1978 | Polczynski | 385/123 X |
| 4,106,847 | 8/1978 | Arnaud | 385/123 X |
| 4,307,938 | 12/1981 | Dyott | 385/123 |
| 5,206,878 | 4/1993 | Sizer, II | 372/101 |
| 5,265,177 | 11/1993 | Cho et al. | 385/146 X |
| 5,333,232 | 7/1994 | Yanagawa et al. | 385/127 |

*Primary Examiner*—John D. Lee
*Attorney, Agent, or Firm*—Bolesh J. Skutnik

[57] ABSTRACT

An optical fiber includes a transparent core having a generally rectangular cross section covered by a transparent cladding having a generally elliptical outer surface. The rectangular cross section has a width-to-thickness ratio substantially equal to a length-to-width ratio of a laser source such as, for example, a laser diode. The equality of dimensional ratios permits efficient coupling of laser radiation to the transparent core. The rectangular cross section, thus, avoids reduction in energy density at the output end of the fiber core, as occurs when a rectangular output of a solid state laser is coupled to a fiber core having a circular cross section. Embodiments are disclosed having dimensional ratios of from about 2:1 to 20:1 and beyond. The improved dimensional matching permits delivery of radiation from laser diodes at energy densities useful for medical treatments.

12 Claims, 3 Drawing Sheets

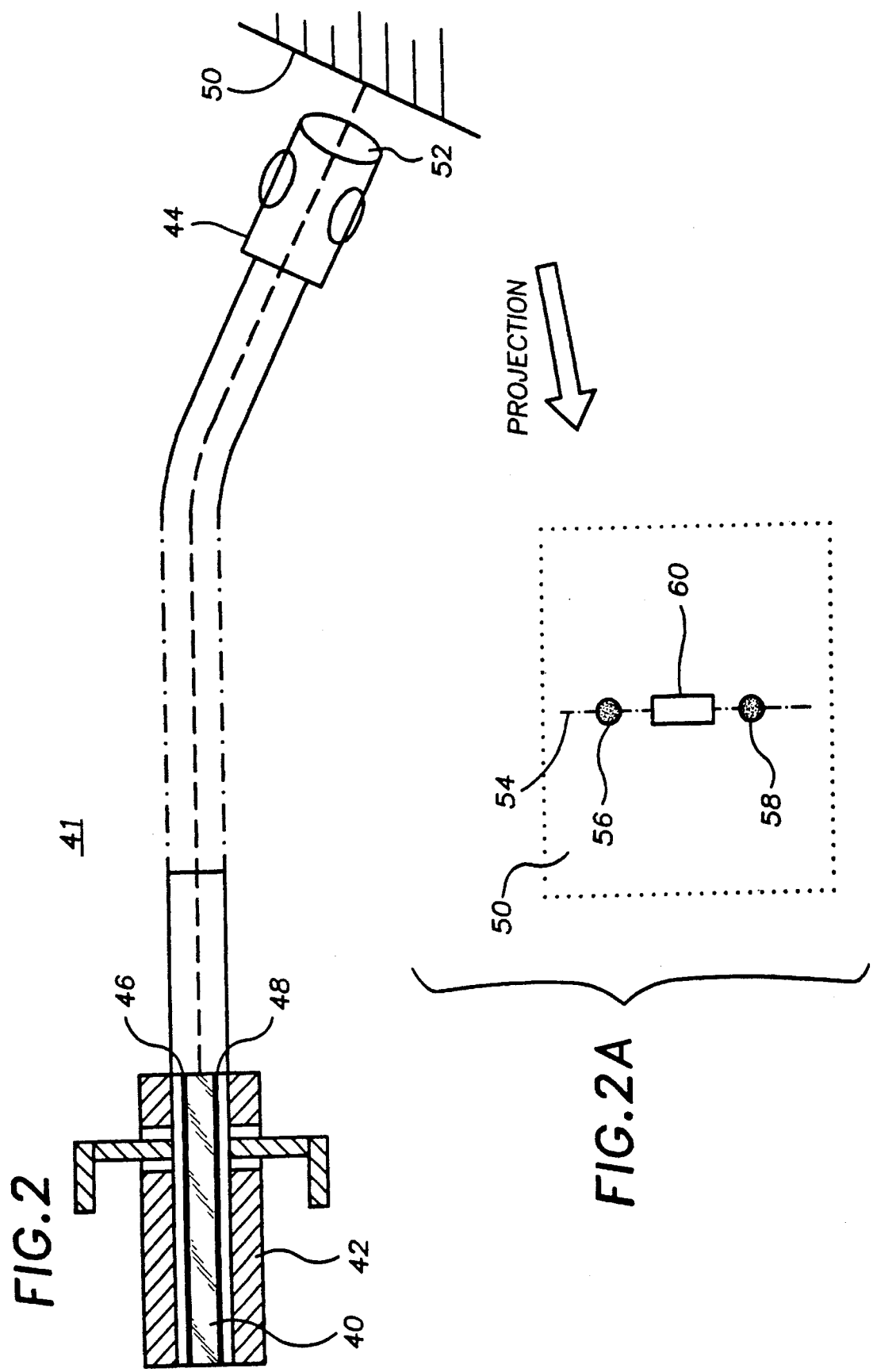

FLAT SURFACED OPTICAL FIBERS AND DIODE LASER MEDICAL DELIVERY DEVICES

BACKGROUND OF THE INVENTION

1. Field of the Invention

The invention relates generally to the class of multimode optical fibers and in particular to a new class wherein the core of the fiber has flat surfaces rather than being round and to their use with diode lasers in medical applications.

2. Information Disclosure Statement

Medical laser devices, of the types used for medical treatments, generally employ a laser, capable of generating a significant amount of optical power, coupled to a fiber optic delivery device for delivering the optical power from the laser source to a treatment site for cauterization or other use.

Present technology offers devices with powerful glass rod, dye or Argon:ion lasers as the source of optical power coupled with a delivery system consisting essentially of a connector, one or more flexible fibers and a distal tip, suitably configured for the intended treatments. A typical optical fiber has a circular core coated with a cladding having an index of refraction lower than that of the fiber core, to redirect light rays attempting to escape the optical fiber core back into the core. The difference in refractive index can be accomplished, for example, by doping the cladding with fluorine or by doping the fiber core with germanium.

Semiconductor laser sources are convenient because of their relatively low cost, and their ability to generate optical outputs of significant power. Present technology offers semiconductor laser sources capable of generating as much as a watt or more of optical power. This output occurs over a generally rectangular area of, for example, about 200 by 10 µm with divergences of 40 and 20 degrees in the respective axis. Effective treatment requires that the available output power be delivered to the treatment site with a certain minimum optical power density (watts/cm$^2$). Conventional optical fibers have a circular cross section. To capture as much optical output power as possible, it is conventional to use an optical fiber having a core diameter substantially equal to the major dimension of a semiconductor laser source (200 µm in the example above). However, the cross sectional area of a 200-µm diameter optical fiber core is about $3.15\times10^4$ µm$^2$, whereas the cross sectional area of the example 200 by 10 µm laser output is about $2.0\times10^3$ µm$^2$. Therefore, the energy density of the rectangularly shaped radiation input to the fiber is transformed by multiple internal reflections within the circular optical fiber core to a generally uniform energy density across the entire output cross section of the optical fiber core. Thus, the input energy density of a one-watt diode laser at the input end of the fiber core (one watt/$(2\times10^{-5})$cm$^2$=50 kW/cm$^2$) is reduced by about a factor of 16 (plus coupling and attenuation losses) to a value less than that required to effect for most medical treatments.

This reduction in output energy density is a main reason why current technology does not use semiconductor laser sources. Increasing the power of the laser source is not feasible for low-cost semiconductor lasers. This has lead to the use of higher-cost laser sources such as, for example, Nd:YAG, Dye, Holmium:YAG, Ar:Ion or other. These lasers, besides being capable of higher output power, have typically circular symmetric emission characteristics, and thus can be easily focused onto the circular input end of a fiber core.

The present state-of-the-art lasers are, however, relatively expensive, complex and maintenance-intensive. These drawbacks limit their use—and, indeed, the whole scope of present-day medical laser practice—essentially to large clinics. With the current availability of laser diodes, new areas can be made accessible, since the laser diodes are small, lightweight and easily configurable into essentially maintenance-free, potentially cheap laser systems, provided that the energy density required for effective medical treatment can be delivered to the treatment site.

Optical methods, including lenses, are only partially effective in correcting the shape mismatch between laser diode output and conventional optical fiber input. At best, a lens is able to equalize the divergences in the two dimensions and to compress the rectangular diode laser output by a ratio of about 2:1 or 3:1, rather than the 10:1 or 30:1 requires for effective coupling of power density to the optical fiber.

Power density, however, is a critical value in medical laser treatments, as it controls the physical effects of the radiation on the tissue. For instance vaporization of tissue can only be achieved above a certain power density threshold.

The above mentioned problems clearly hinder the penetration of laser diodes into the market.

OBJECTS AND SUMMARY OF THE INVENTION

It is an object of the present invention to provide a technique which solves the problems of the prior art.

It is a further object of the present invention to produce optical fibers which can optimally couple with diode lasers.

It is a still further object of the present invention to create medical laser delivery devices with improved characteristics that are better suited for diode lasers, especially in maintaining the higher power densities of the latter.

It is yet another object of the present invention to provide methods of manufacturing preforms suited to draw the fibers with flat surfaced core cross sections for the medical laser delivery devices.

It is a further object of the invention to provide suitable connection and other means to form diode laser-fiber-systems.

Briefly stated, the present invention provides an optical fiber with a transparent core having a generally rectangular cross section covered by a transparent cladding having a generally elliptical outer surface. The rectangular cross section has a width-to-thickness ratio substantially equal to a length-to-width ratio of a laser source such as, for example, a laser diode. The equality of dimensional ratios permits efficient coupling of laser radiation to the fiber core. The rectangular cross section, thus, avoids reduction in energy density at the output end of the ceramic core, as occurs when a rectangular output of a solid state laser is coupled to a fiber core having a circular cross section. Embodiments are disclosed having dimensional ratios of from about 5:1 to 20:1 and beyond. The improved dimensional matching permits delivery of radiation from laser diodes at energy densities useful for medical treatments.

According to an embodiment of the invention, there is provided an optical fiber comprising: a transparent core, a transparent cladding surrounding the transparent core, the transparent cladding having a refractive index lower than that of the transparent core, and the transparent core having a generally rectangular cross section, whereby the optical fiber is effective for efficiently receiving radiation from a source having a generally rectangular output shape.

According to a feature of the invention, there is provided A medical laser delivery device comprising: at least one optical fiber with a core and a cladding, the core having a generally rectangular cross section, means for coupling radiation from a laser device to said core, whereby an energy density of radiation input to the optical fiber from the laser device is substantially preserved at an output of the optical fiber, and means for delivering radiation from the output to a treatment site.

According to a further feature of the invention, there is provided a medical laser diode-optical fiber system comprising: at least one laser diode, the laser diode having a generally rectangular output having a length-to-width ratio, an optical fiber having a transparent core, a transparent cladding surrounding the core, the core having a width-to-thickness ratio, the width-to-thickness ratio being substantially equal to the length-to-width ratio, means for coupling the output to an input of the core, whereby the substantial equality between dimensional ratios of the output and the core permit efficient coupling of the output to the input of the core, and means for delivering an output of the core to a treatment site.

According to a further feature of the invention, there is provided a medical laser diode-optical fiber system comprising: at least one laser diode, the laser diode having a generally rectangular output having a length-to-width ratio, an optical element to reshape the rectangular output so as to equalize divergences associated with the length and width dimensions, an optical fiber having a transparent core, a transparent cladding surrounding the core, the core having a width-to-thickness ratio, the width-to-thickness ratio being substantially equal to the length-to-width ratio, means for coupling the output to an input of the core, whereby the substantial equality between dimensional ratios of the output and the core permit efficient coupling of the output to the input of the core, means for delivering an output of said core to a treatment site wherein a generally rectangular pattern of laser energy is projected on the treatment site, the rectangular pattern having a major and a minor axis, and means for projecting on the treatment site at least one indicator of the location of the major axis, whereby an operator is guided in positioning the pattern for effective treatment.

The above, and other objects, features and advantages of the present invention will become apparent from the following description read in conjunction with the accompanying drawings, in which like reference numbers in different drawings denote like items.

BRIEF DESCRIPTION OF DRAWINGS

FIG. 2 shows another preferred embodiment with a cutting hand piece.

FIG. 2A shows an image projected from the hand piece of FIG. 2.

DETAILED DESCRIPTION OF PREFERRED EMBODIMENTS

Figure 1:
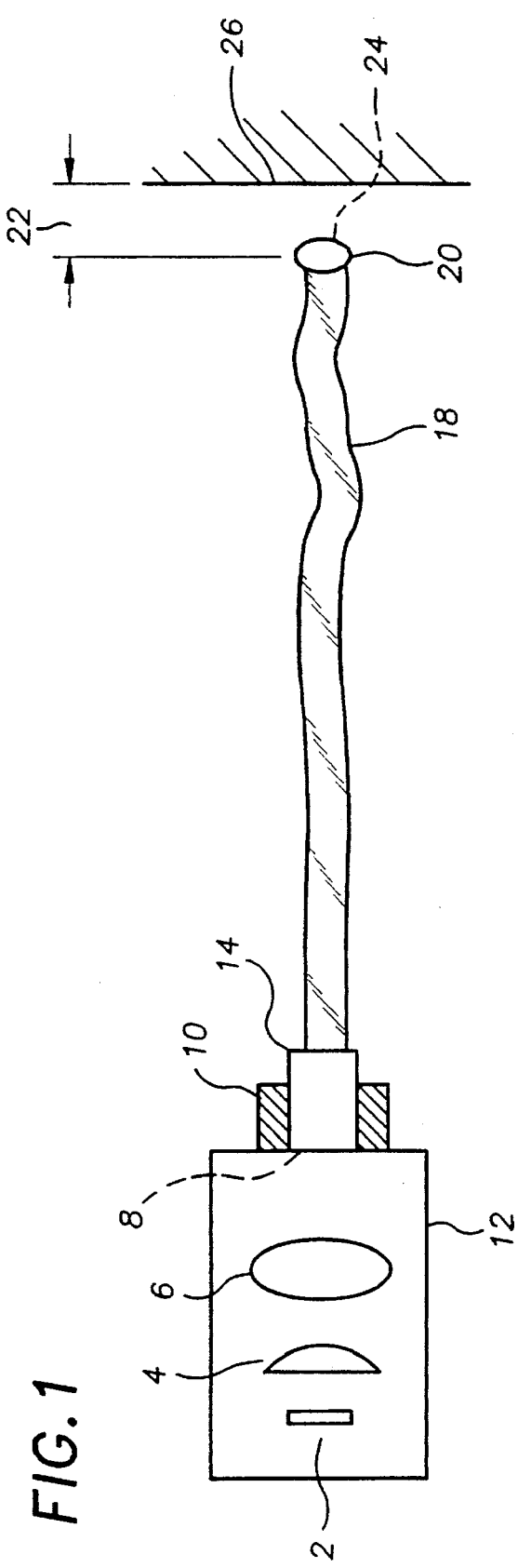
FIG. 1 shows a simple diode laser-fiber-system as one embodiment of the present invention.

Referring to FIG. 1, in a delivery system 1, a single laser diode 2 with an emission cross section of 200 by 3 µm and divergences of 20 and 40 degrees respectively is affixed with a cylindrical lens 4 to reduce the divergence in the small dimension to 20 degrees. A further lens 6 projects the beam on the fiber input end 8. An adapter 10 in the laser housing 12 receives the delivery systems input connector 14.

Figure 1A:
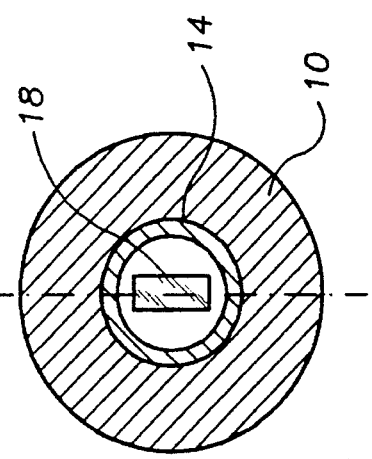
FIG. 1A depicts a cross sectional view of the connector/adapter sub assembly from FIG. 1.

Referring also to FIG. 1A, connector 14 and the adapter 10 fit together in a fixed angular position 16. Fiber 18 in delivery system 1 has a generally rectangular core cross section, as for example, a core cross section of 200 by 10 µm (i.e. a ratio of major/minor axes of 20:1) and a numerical aperture of 0.2, thereby avoiding reduction in optical energy density through shape mismatch at the input end. At output end 24, a small spherical lens 20 reduces divergence of the beam to give the power density desired. Lens 20 is positioned at working distance 22 from a tissue surface 26, where the beam achieves the desired medical effect.

The superiority of this arrangement compared to the present state-of-the-art, which typically use a fiber with a 200 µm circular core cross section, is evident. Only a strip of the input end of the circular core is irradiated by the rectangular laser output. In travelling down the optical fiber core, these rays become distributed over the full circular cross sectional area and the optical energy density of the laser diode is irretrievably and significantly reduced.

With a laser output of 200 by 10 µm, the optical energy density of a system using a 200 µm circular cross section optical fiber core versus an optical fiber having a cross section of 200 by 10 µm at an equal distance to the tissue are related to each other as:

$$(200^2 \times \pi/4)/(200 \times 10) = 15.7 \tag{1}$$

This expression shows that an optical fiber according to the present invention delivers over ten times more optical energy density to ablate tissue than achievable with a conventional circular cross section optical fiber, using the same laser source. This makes a semiconductor laser having an output power of about one watt, as effective as the higher-powered and substantially more costly lasers listed above.

Fiber 18 can have a core that is doped and a cladding that is undoped or vice versa. That is, the dopant can be part of the core or part of the cladding.

In some applications, it may be satisfactory for fiber 18 to have a rectangular cross sectional shape having a width to thickness ratio of as little as 5:1. In more preferred embodiments, the width to thickness ratio is about 10:1 and more preferably about 20:1, or more.

Referring to FIG. 2, in another preferred embodiment, a delivery device 41 contains a connector 42, a fiber 40 with a rectangular core cross section and a hand piece 44. Hand piece 44 incorporates two further fibers 46 and 48. Fibers 46 and 48 have low numerical apertures (e.g. 0.1) that transport visible aiming beams from connector 42 to an output end 52 of delivery device 41. Aiming beams are then projected onto tissue 50, where they make a pair of spots 56 and 58 that delineate a main output beam longitudinal axis 54. This delineation indicates visually, to a surgeon using a device of the present invention, the optimum cutting treatment of the laser beam, a spot 60.

In addition to the embodiment described above, a plurality of diodes can be combined to feed a single rectangular optical fiber core. For example, if four diodes are combined, a final fiber geometry of 200 by 40 μm may be optimal.

While it is possible to manufacture rectangular plastic clad silica (PCS) fibers (for example, by drawing and coating a quartz rod polished and etched down to the equivalent geometry), it is very difficult, if not impossible, to manufacture 200 by 10 μm core PCS fibers in this manner. The fibers obtained with this technique tend to be fragile, and they lack the necessary strength and handling characteristics. Using conventional CVD techniques, it is also close to impossible to achieve preforms or fibers with the required dimensions. This difficulty results from the fact that the manufacturing processes have been designed for drawing circular or near circular geometries.

The inventor has discovered that a conventional plasma deposition process for coating a cladding on a glass substrate tends to build up cladding material faster on broad surfaces than on narrow surfaces, and it tends to build up cladding on flat sufaces than it does on corners. As a result, the inventor has found that, starting with a meter long core preform having a rectangular cross section of, for example, 20 mm by 1 mm, plasma coating produces a clad preform with a generally elliptical outer dimension. As the coating process proceeds, the outer dimension becomes less elliptical, and at some point will become substantially circular. Elliptical preforms are suitable for drawing into fibers on conventional optical fiber draw tower equipment. A preform with core dimensions, as described above, can easily be drawn into optical fiber with fiber core dimensions of 200 by 10 μm. We have observed that the original rectangular shape, and the width to thickness ratio, of the core preform are both accurately preserved in the final optical fiber core.

Coupling efficiency of laser output to fiber input is improved when there is a good match between the fiber core dimensions and the laser output dimensions, and between the divergence of the laser output and acceptance angle of the optical fiber. Where the divergence of the laser output is significantly different in its two dimensions, an optical element such as a cylindrical lens, may be used to reshape the laser output so that the divergence in the smaller dimension is substantially equal to that of the larger dimension. In general, we have found significant improvement in coupling efficiency with a width-to-thickness ratio of as little as 2:1. Better performance is obtained with a width-to-thickness ratio of at least 4:1. For effective coupling to a single laser diode, best coupling is obtained with a width-to-thickness ratio of 20:1. In some case, it is desirable to use a multstripe diode laser, or a stack of two or more diode lasers, for even greater energy input into the fiber. To accomodatethis, the width, thickness, or both may have to be increased by the required amounts.

Figure 4:
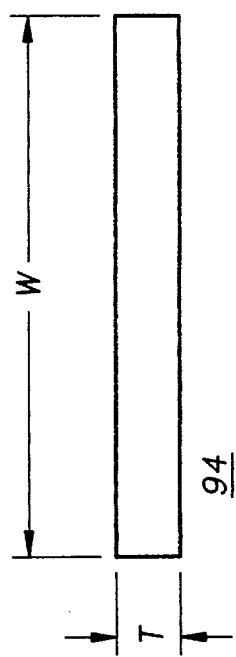
FIG. 4 illustrates a preform shape prior to depositing the cladding layer.

Referring now to FIG. 4, a core preform consisting of a quartz bar 94, having a width-to-thickness ratio equal to the width-to-thickness ratio desired in the finished core, but geometrically much bigger (for example, 20 mm by 1 mm) is inserted into a conventional deposition machine (not shown) where it is coated with a substantial layer of fluorine-doped silica. The deposition is faster on the broader flat surfaces than on the side surfaces.

Figure 3:
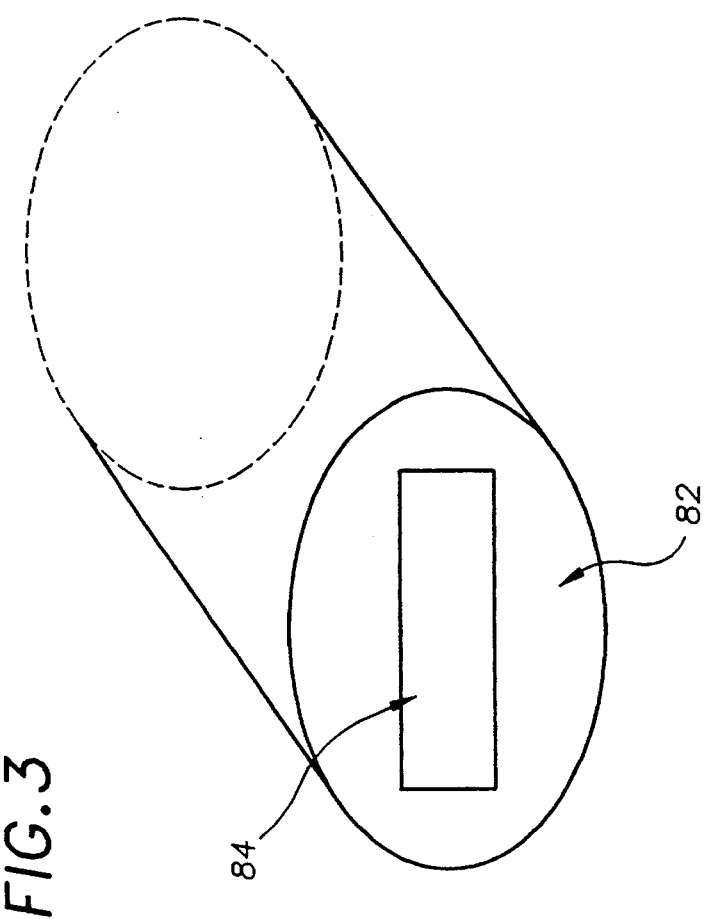
FIG. 3 depicts the cross section of the core and cladding of the new optical fibers. In normal use additional coatings would be applied over the cladding for improved handling and for protection.

A preform made by this process can then be used to manufacture the fiber. Or the preform can be over collapsed with a tube to enlarge the cross section further. Referring also to FIG. 3, the resulting fiber, with its rectangular core 84 and elliptical cladding 82, is strong and stable, as required.

The conventional plasma process for cladding deposition was modified somewhat to obtain fibers with strong and stable properties. The modifications included a lower deposition temperature (for example, 1000° to 1300° C.), suspending the preform vertically in the deposition machine, and rotatng the preform during plasma deposition. Suspending the preform vertically avoids bending of the long thin preform during deposition of cladding. Rotating the preform as cladding is built up and using a lower deposition temperature reduces warping of the preform and enhances the smooth deposition of the cladding on the preform. The build up of cladding on the preform (greater on broad surfaces, less on narrow surfaces, least on corners) was further enhanced by maintaining a proprietary plasma power distribution across the cross sectional plane within the depostion machine.

Having described preferred embodiments of the invention with reference to the accompanying drawings, it is to be understood that the invention is not limited to the precise embodiments, and that various changes and modifications may be effected therein by one skilled in the art without departing from the scope or spirit of the invention as defined in the appended claims.

What is claimed is:

1. An optical fiber comprising:

a transparent core;

a transparent cladding surrounding said transparent core;

said transparent cladding having a refractive index lower than that of said transparent core;

said transparent core having a generally rectangular cross section, whereby said optical fiber is effective for efficiently receiving radiation from a source having a generally rectangular output shape; and said rectangular cross section has a ratio of dimensions at least 5:1.

2. An optical fiber according to claim 1, wherein said cladding has a generally elliptical exterior.

3. An optical fiber according to claim 1, wherein said cladding has a generally round exterior.

4. An optical fiber according to claim 1, wherein said ratio of dimensions is greater than 10:1.

5. An optical fiber according to claim 1, wherein said ratio of dimensions is greater than 20:1.

6. An optical fiber according to claim 1, wherein said rectangular cross section has dimensions substantially equal to dimensions of an image of a radiation source at an input face of said fiber.

7. A medical laser delivery device comprising:

at least one optical fiber with a core and a cladding;

said core having a generally rectangular cross section;

means for coupling radiation from a laser device to said core;

whereby an energy density of radiation input to said optical fiber from said laser device is substantially preserved at an output of said optical fiber; and means for delivering radiation from said output to a treatment site.

8. A medical laser delivery device according to claim 7, wherein said laser device further comprises at least one laser diode.

9. A medical laser diode-optical fiber system comprising:

at least one laser diode, with said laser diode having a generally rectangular output having a length-to-width ratio;

an optical fiber having a transparent core and a transparent cladding surrounding said core;

said core having a width-to-thickness ratio;

said width-to-thickness ratio being substantially equal to said length-to-width ratio;

means for coupling said output to an input of said core, whereby the substantial equality between dimensional ratios of said output and said core permit efficient coupling of said output to said input of said core; and means for delivering an output of said core to a treatment site.

10. A medical laser diode-optical fiber system according to claim 9, wherein said laser diode output has a divergence associated with said length dimension which is different than a divergence associated with said width dimension;

further comprising an optical element between said laser diode and said optical fiber;

said optical element reshaping said laser diode output and thereby equalizing said divergences; and wherein said width-to-thickness ratio of said fiber core is substantially equal to said reshaped laser diode output.

11. A medical laser diode-optical fiber system according to claim 9, wherein said means for delivering an output of said core to a treatment site involves projecting a generally rectangular pattern of laser energy on said treatment site;

said rectangular pattern having a major and a minor axis; and further comprising means for projecting on said treatment site at least one indicator of the location of said major axis, whereby an operator is guided in positioning said pattern for effective treatment.

12. A medical laser diode-optical fiber system according to claim 11, wherein said at least one indicator includes first and second spots of visible light as points on said major axis.

\* \* \* \* \*